United States Patent [19]
Cotrel

[11] Patent Number: 4,815,453
[45] Date of Patent: * Mar. 28, 1989

[54] DEVICE FOR SUPPORTING THE RACHIS

[75] Inventor: Yves P. C. A. Cotrel, Taden, France

[73] Assignee: Societe de Fabrication de Materiel Orthopedique (SOFAMOR), Berck-Plage, France

[*] Notice: The portion of the term of this patent subsequent to Feb. 10, 2004 has been disclaimed.

[21] Appl. No.: 938,434

[22] Filed: Dec. 5, 1986

Related U.S. Application Data

[63] Continuation-in-part of Ser. No. 599,558, Apr. 12, 1984, Pat. No. 4,641,636.

[30] Foreign Application Priority Data

May 4, 1983 [FR] France .................... 83 07450

[51] Int. Cl.$^4$ .............................................. A61F 5/00
[52] U.S. Cl. ................................. 128/69; 128/92 R; 128/92 YM
[58] Field of Search ........... 128/69, 75, 92 YM, 92 R, 128/92 E

[56] References Cited

U.S. PATENT DOCUMENTS

| | | | |
|---|---|---|---|
| 4,047,523 | 9/1977 | Hall | 128/69 |
| 4,116,235 | 9/1978 | Fuhr et al. | 128/69 |
| 4,409,968 | 10/1983 | Drummond | 128/69 |
| 4,422,451 | 12/1983 | Kalamchi | 128/69 |

FOREIGN PATENT DOCUMENTS

| | | | |
|---|---|---|---|
| 3032237 | 3/1982 | Fed. Rep. of Germany | 128/69 |
| 2244446 | 4/1975 | France . | |
| 2545350 | 8/1985 | France . | |
| 624615 | 9/1978 | U.S.S.R. | 128/69 |
| 654251 | 3/1979 | U.S.S.R. | 128/69 |
| 2096465 | 10/1982 | United Kingdom | 128/69 |

OTHER PUBLICATIONS

"Spine Instrumentation", Zimmer Catalog, p. D67, Feb. 1973.
Orthopedic Biomechanics: Keys to the Skeleton, David A. Hoeltzel, *Mechanical Engineering*, (May, 1986).
Surgeons See New Operation for Correcting Spinal Curvature, The Courier-Journal, Sep. 18, 1984, NKC Hospitals Host Historic Spine Surgery NKC News.
New Surgery Will Rid Some Adolescents of Back Braces, Today's Health, Nov. 1984.
A Patient's Tale: Once Was Not Enough, Discover, Dec. 1984.
The Latest Wrinkle in Correcting Scoliosis, American Journal of Nursing, Jan. 1985.
Cotrel-Dubousset Instrumentation for Correction Scoliosis Outlined, Surgical Technique, Interviews, Feb. 1985.
A French Doctor Pioneers a Way to Correct Crooked Spines, People Magazine, Apr. 29, 1985.
Scoliosis: A 30-Second Check-up, McCall's Magazine, May 1985.
New Method of Surgical Treatment for Scoliosis Backtalk, Summer, 1985.
Cotrel-Dubousset Instrumentation for Scoliosis Backtalk, Summer 1985.
Innovative Surgery Has Alpine Girl Walking Tall, The Daily Californian, Sep. 28, 1985.
Spinal Curvature Corrected, The San Diego Union, Monday, Oct. 7, 1985.
Strasbourg: Une Reunion Organisee Par les Laboratories Specia Chirurgie des Scolioses: Apres l'intervention de Harrington celle de Cotrel, Le Uuotidien Du Medecin, Mardi 15, Oct. 1985.

(List continued on next page.)

Primary Examiner—Edgar S. Burr
Assistant Examiner—Moshe I. Cohen
Attorney, Agent, or Firm—Fisher, Christen & Sabol

[57] ABSTRACT

The invention relates to a device for supporting the rachis comprising at least one pin and at least two anchoring members attached thereto. According to the invention, said device is characterized in that the pin is of constant cross-section throughout its length and presents a rough surface, and in that the anchoring members are provided with pressure means cooperating with said pin. The invention finds applications in the straightening and/or support of a rachis, especially in preparation for an arthrodesis.

25 Claims, 6 Drawing Sheets

OTHER PUBLICATIONS

Standing Straight, Discover Dec. 1984.

Essais Comparatifs de Tenue a la Fatigue sur des Tiges Chirurgicales soumises au flambage ou a la flexion repetee Rapport, Laboratoire National D'Essais, Jun. 30, 1982.

Report: Breaking-point and Deformation Study under Loads of Metallic Equipment (to be implanted in spine surgery), Feb. 27.

Universal Instrumentation (CD) For Spinal Surgery, Stuart, 1985.

Universal Instrumentation (CD) for Spinal Surgery, Sofamor (SFM).

5th Annual Kosair Children's Spine Symposium Hands-on Presentations by French Surgeons Yves Cotrel and Jean Dubousset, Dec. 2 & 3, 1985.

Cotrel- Dubousset Instrumentation for Correction of Scoliosis Outlined Surgical Technique, Orthopedics Today, Mar. 1985.

DEVICE FOR SUPPORTING THE RACHIS

This is a continuation-in-part of my prior U.S. patent application, Ser. No. 599,558, filed on Apr. 12, 1984, now U.S. Pat. No. 4,641,636.

BACKGROUND OF THE INVENTION

The present invention relates to a device for supporting the rachis, installed by surgery. Said device can be used just for consolidating a rachis which needs to be consolidated (accidental fracture, for example) or else for correcting and supporting a rachis suffering from curvatures (scoliosis, kyphosis, for example). Although the device according to the invention is suitable for these two types of applications as well as others, it is described hereinafter primarily with reference to the surgical treatment of lateral curvatures of the spine.

Scoliosis, it is known, is a lateral curvature of the spine, together with rotation of certain vertebra about their axis. Abnormal spinal flexure, resulting from said lateral curvature, is generally defined from specific points, namely the upper and lower extreme vertebra between which said abnormal flexure is found, and the vertebra or vertebra at the top thereof. Said upper and lower extreme vertebra are those which have pivoted the least about their axes, but they are on the other hand, those most inclined on the median longitudinal axis, and their planes determine between them the angle of scoliotic curvature. The apical vertebra or vertebra are those farthest from said median axis of the torso; they are slightly inclined or not inclined at all with respect to said axis but, on the other hand, they are those which suffer the strongest rotation about their axis.

When the scoliotic curvature angle exceeds a certain threshold (around 50°), it becomes necessary to consider treating the scoliosis by surgery, said surgical treatment being called arthrodesis and consisting in welding together all the vertebra of the scoliotic curvature, after a maximum correction thereof, by straightening and opening.

Such correction may be accomplished before surgery by continuous traction of the rachis or by using corrective plasters. Said correction however, is completed and finalized during surgery. To this effect, a solid prop member is placed in the concavity of the rachidial curvature at least, said prop member consolidating the resulting correction and being able to strengthen the bone joint obtained by arthrodesis.

One instrumentation called the "HARRINGTON instrumentation" is already known to perform this. Said instrumentation consists of an elongation system, designed to be inserted in the concavity of the curvature, and of a compression system designed to be optionally inserted on the convex side. Often in fact, only the elongation system is used.

Said elongation system comprises two metallic anchoring members, of the hook type, resting against the extreme vertebra of the curvature, and a metallic pin acting as a support, and serving to keep the hooks one apart from the other, and as a result, to correct the scoliotic curvature. Said metallic pin, of circular cross-section, is provided at its lower part with a shoulder member, and at its upper part, with a notched portion, and it traverses the said hooks. The lower hook is fastened on the lamina of the lower extreme vertebra of the curvature and the metallic pin rests on said lower hook via the said shoulder member. The upper hook, which is fitted over the said pin, is placed under the facet of the upper extreme vertebra of the curvature and by external operations of traction (using for example retractors which rest aginst the notches of the upper pat of the rod), the upper hook is drawn apart from the lower hook. Said upper hook goes past the notches of the notched portion of the pin, successively, and when the required correction is obtained, a locking device (such as a clip for example) is inserted between the upper hook and the notch nearest thereto.

The compression system is composed of transverse hooks traversed by a threaded pin provided with nuts. The upper hooks are fastened on the transverse processes of the vertebra, whereas the lower hooks rest under the transverse processes or under the lamina of the vertebra of the curvature which are close to the lower extreme vertebra. A nut is associated with each hook, and the required compression is obtained by actuating said nuts.

After fitting the instrumentation into place, an arthrodesis is carried out and the patient is made to wear a corset for support for a period varying between 6 and 12 months.

The type of instrumentation, although widely used, presents a number of disadvantages, which are that:

(a) the opening of the curvature cannot be adjusted in continuous manner, but on the contrary in step-wise manner, each adjusting step being constituted by a notch of the notched portion of the elongation system. As a result, final adjustment of the opening of the rachis is achieved, not absolutely accurately, but only to within the nearest notch;

(b) opening of the curvature is achieved by applying very localized pressure at the level of the two extreme vertebra of the curvature only, so that the pressure exerted on said vertebra is very strong;

(c) the hooks of the elongation system, in particular, can pivot about the metallic pin of said system, thus enabling them to move with respect to their initial positioning;

(d) no direct re-centering action towards the axis of the torso is exerted by the instrumentation;

(e) no real action of derotation is exerted on the apical vertebra or vertebrae;

(f) despite prolonged postsurgical support, breakage of the rod of the elongation system occurs, at the junction of the smooth parts with the notched parts, in 2.5 percent of cases.

SUMMARY OF THE INVENTION

It is the object of the present invention to overcome these disadvantages by developing a strong enough instrumentation to do away with the long postsurgical setting periods in a plaster or corset, during the vertebral synostosis.

This object is reached according to the invention with a device for strengthening the rachis, of the type comprising at least one pin and two anchoring members able to rest on vertebra of said rachis and to be fixed in position on said pin, which device is remarkable in that said pin is of substantially constant cross-section throughout its length and has a rough surface, and in that said anchoring members are provided with pressure means cooperating with said pin.

In a preferred embodiment, the device for strengthening the rachis comprises at least one pin and at least two hooked anchoring members able to rest on vertebra of the rachis and to be fixed in position on the pin, the pin being of constant cross-section throughout its length and having a rough surface, with the anchoring members comprising a body with a through hole for the free passage of the pin the hole opening onto a groove which can be traversed by the pin, and the anchoring members each being associated with at least one locking element slidable on the pin, upon which it can be locked in position by means of a pressure screw transverse to the pin and able to engage with the rough surface to fix the locking element in position, wherein the anchoring members can be interlocked with the associated locking elements by wedging.

It is thus possible, due to the cooperation of the pressure means of said anchoring means with said pin, and to the surface condition of the latter, to adjust continuously and accurately the position of said anchoring members and, in doing so, adjust the opening of the scoliotic curvature. The invention further permits the interlocking of the anchoring members of the pin, so that no rotation is possible after actuating said pressure means. It also permits the surgeon to multiply at will the anchoring members and to distribute them in such a way that each vertebra of the curvature is fixed in the required corrected position. Since the pin has a constant cross-section, it no longer has any weak points, can easily and safely be bent, and breakage is prevented.

The pin can be milled, knurled or turned in order to have the required roughness of surface. It will be noted that such roughness, in the case of arthrodesis, helps the adherence of the neoformed bone to the pin, so that the pin becomes firmly locked with the blended bone area.

Further in accordance with the present invention, a method of installing a device for strengthening a deformed rachis having a concave and convex side in the transverse plane is provided, the device comprising a single pin of substantially constant cross-section which has a surface roughened by milling or turning and at least two hooked anchoring members mounted thereon, each having means to selectively fix the anchoring members comprising a pressure screw transverse to the pin, comprising the steps of:

(a) attaching the anchoring members to vertebra on the convex side of said rachis;

(b) inserting the pin into the lowest of the anchoring members on the convex side of the rachis;

(c) manipulating the pin so as to substantially straighten the rachis, derotate at least some of the vertebra, and insert the pin into the remaining anchoring members on the convex side of the rachis; and (d) fixing all the anchoring members in place on the pin by tightening the pressure screws to prevent sliding and rotational motion on the pin.

Further in accordance with the invention, a method is provided for installing a device as described above on the concave side of a deformed rachis as described, comprising the steps of:

(a) attaching the anchoring members to vertebra on the concave side of said rachis;

(b) inserting the pin into the lowest of the anchoring members on the concave side of the rachis;

(c) manipulating the pin and applying elongational force to the anchoring members so as to substantially straighten the rachis, derotate at least some of the vertebra, and insert the pin into the remaining anchoring members on the concave side of the rachis; and (d) fixing all the anchoring members in place on the pin by tightening the pressure screws to prevent sliding and rotational motion on the pin.

DESCRIPTION OF THE INVENTION

The invention will be more readily understood on reading the following description with reference to the accompanying drawings, in which.

DETAILED DESCRIPTION OF THE INVENTION

Figure 1:
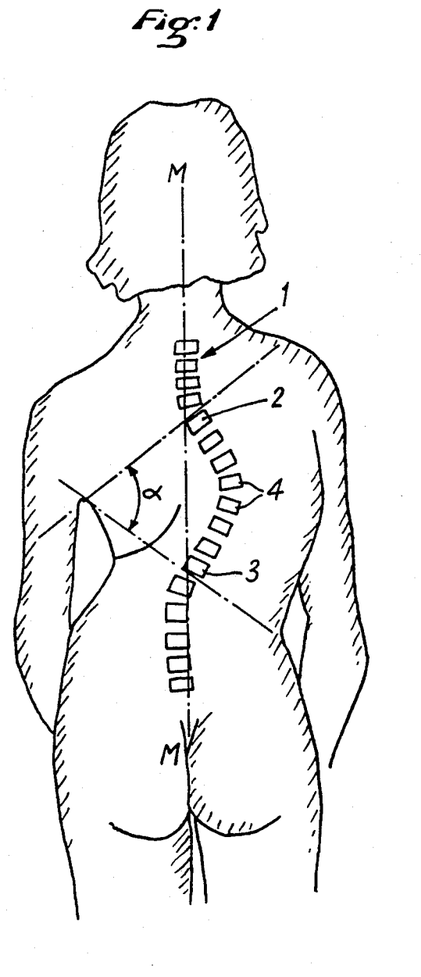
FIG. 1 diagrammatically illustrates the back of a patient suffering from scoliosis.

Referring first to FIG. 1, this diagrammatically shows the back of a patient suffering from scoliosis, assuming that the spine 1 is visible. The vertebra are illustrated by small rectangular or trapezoidal shapes.

This patient has a scoliosis causing a spinal curvature towards the right. The scoliotic curvature can be defined according to upper 2 and lower 3 extreme vertebra of the curvature, and to vertebra 4 situated at the apex of said curvature. It will be noted that vertebra 2 and 3 are those which are the most inclined on the median longitudinal axis MM of the body, whereas vertebra 4 are those farthest from said axis. The angle formed by the planes of vertebra 2 and 3 is therefore a characteristic of the scoliotic curvature. As already indicated hereinabove, when angle exceeds a certain threshold (about 50°), it becomes necessary to resort to arthrodesis and to install a support for the rachis.

Figure 2:
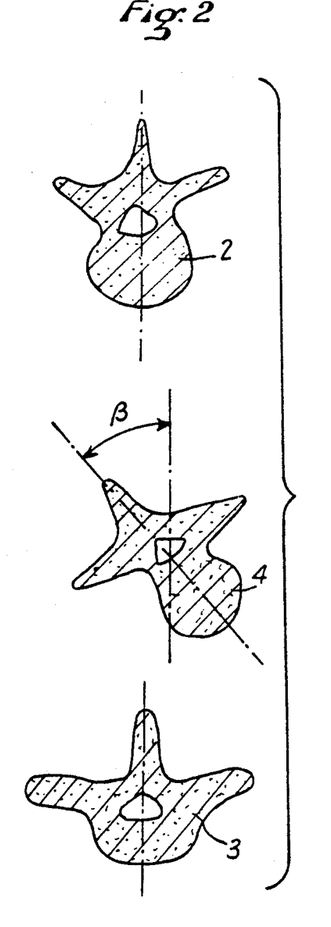
FIG. 2 illustrates the relative rotation of the vertebra of a scoliotic rachis.

Also, and as illustrated in FIG. 2 showing diagrammatical views of each one of vertebra 2, 3 and 4, the vertebra 4 at the apex of the curvature is subjected to a rotation about its axis of amplitude, due to scoliosis.

Figure 3:
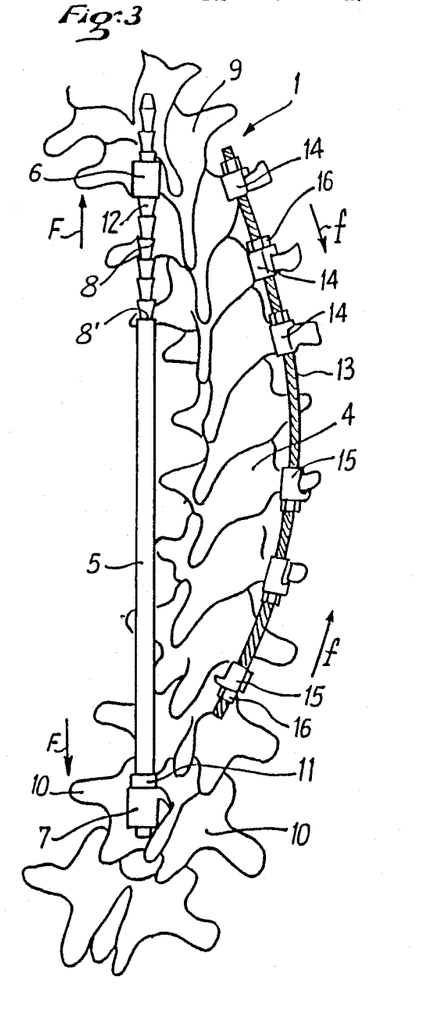
FIG. 3 shows a known instrumentation used for surgical correction of scoliosis.

FIG. 3 illustrates the known method and instrumentation of HARRINGTON for correcting and strengthening a rachis, mentioned hereinabove. The elongation system comprises a cylindrical metal pin 5 able to cooperate at its two ends with anchoring devices 6 and 7. One of the ends 8 of the pin 5 is notched so as to enable adjustment of the distance between the anchoring devices 6 and 7.

Normally, the upper anchoring member 6, namely that designed to be fixed next to the upper part of the rachis, is fastened to a thoracic vertebra 9 and its hook (not shown in FIG. 3) is facing upwardly and so shaped as to be insertable between the spinalis and a transverse process of said vertebra, between the upper and lower articular facets, said hook penetrating into the interarticular space and resting against the upper vertebra at that level.

In like manner, the lower anchoring member 7, namely that designed to be fixed on the side of the lower part of the rachis, is often resting on a lumbar vertebra 10. To this effect, its hook (not clearly shown in FIG. 3) is facing downwardly and rests on the vertebral lamina of said vertebra between the process and articular mass. The sliding movement of the lower anchoring member along pin 5 is limited upwards by a shoulder member 11 integral with said pin. vertebra 9 and 10 of FIG. 3 could be the extreme vertebra 2 and 3 of FIG. 1.

After positioning the anchoring members 6 and 7 on their respective vertebrae, said members are drawn apart as indicated hereinabove (arrows F), in order to reduce the scoliotic curvature. When the reduction is completed, the resulting spacing of the anchoring members is maintained by fitting in a locking clip 12 between a notch of part 8 and anchoring member 6.

FIG. 3 clearly shows the disadvantages a, b, c, and f, mentioned hereinabove as regards the elongation system and in particular the risk of the pin 5 breaking at the joining point 8' of the notched part 8 with the rest of the pin.

The instrumentation of HARRINGTON can further comprise a compression system composed of a flexible threaded pin 13, on which slide three upper anchoring members 14 and three lower anchoring members 15. Said anchoring members 14 and 15 each rest on a vertebra of the curvature of rachis 1 and ar pressed against it by way of nuts 16 screwable on said threaded pin 13, so that they perform a compression action (Arrows F).

It is thus obvious that, even with a compression system 13 to 16, the known instrumentation illustrated in FIG. 3 performs no direct re-centering action towards axis M—M and no derotation of vertebra 4 at the top of the curvature (point d and e above).

Figure 4:
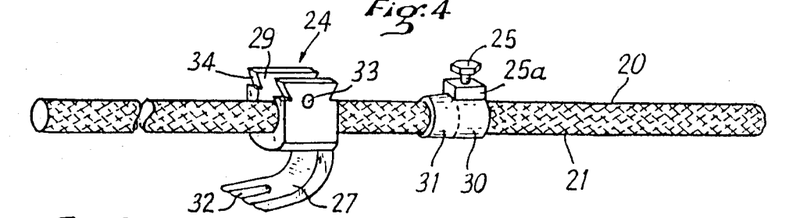
FIGS. 4 to 9 illustrate the instrumentation according to the invention.
Figure 5:
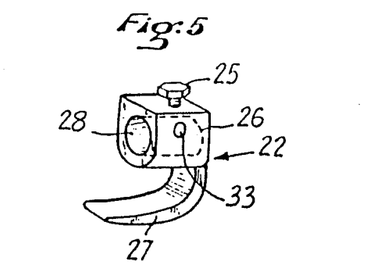

In order to overcome disadvantages a, c, and f inherent in the known instrumentation, the present invention has provided an improved support pin 20 to replace pin 5. As illustrated in FIG. 4, support pin 20 according to the invention is of substantially constant cross-section throughout its length (therefore has no weak points) and its surface is provided with a multitude of asperities 21, obtained for example by milling, knurling or turning. Preferably the pin surface is knurled, providing asperities or projections having a diamond or pyramidal shape. Anchoring members 22, 23 or 24 (see FIGS. 4, 5 and 6) are also provided, which members can be fastened at any point on pin 20, by means of pressure screws 25. The pressure screws 25 bite into the rough surface of pin 20 when tightened, thus fixing the anchoring member firmly in position and preventing both sliding and rotational motion of the member upon the pin.

Figure 7:
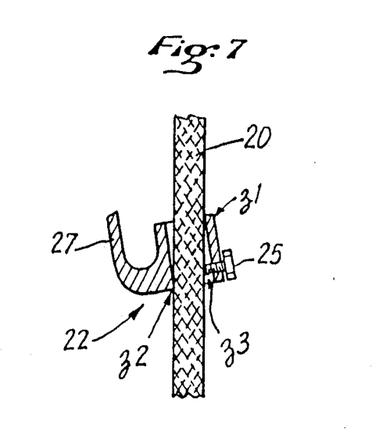

Anchoring member 22 (FIG. 5) comprises a body 26 with which is associated a hook 27. Said body 26 is provided with a through hole 28, whose diameter is sufficient to allow said member 22 to slide freely along pin 20, when said pin traverses hole 28. A screw 25 whose end issues into hole 28, is screwed into said body 26. Thus, as illustrated in FIG. 7, anchoring member 22 can be fixed in any position on pin 20, by screwing in screw 25, and after being placed on said pin 20 by any end thereof.

The loading of member 22 causes same to pivot with respect to pin 20 (as exaggeratedly illustrated by way of example in FIG. 7) so that contact between pin 20 and said member is made in three separate areas z1, z2 and z3 when screw 25 is tightened. The fastening of anchoring member 22 on pin 20 is then perfect, both in longitudinal position and in the pivoting movement of said pin, so that it can be used both in traction and in compression as well as in any rotational position, even with a single pin. The screw 25 can later be loosened and re-tightened if adjustments are necessary or if a more permanent installation is desired, can be tightened and broken, clipped or sawed off substantially flush with the surface of the anchoring member.

Figure 6:
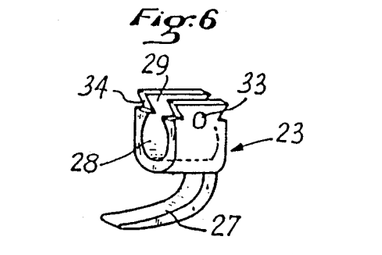

FIGS. 4 and 6 show anchoring members 23 and 24 with open bodies. Indeed, since according to the invention, the anchoring members can be firmly fixed in any points of the pin 20, it is possible to multiply their numbers along said pin in order to increase the number of holds along the rachis; it is therefore advantageous to be able to position said anchoring members along said pin in a non-permanent manner, before installing the pin. To this effect, said anchoring members 23 and 24 comprise a novel groove 29 permitting the introduction of the pin 20 into hole 28 which is open to the outside. Members 23 and 24 can thus be fitted at any moment in any position on pin 20. This combination of open and closed anchoring members permits great flexibility in placement of the hooked members along the rachis, installation of the pins, and manipulation of the pin to correct various spinal deformities. With each member 23 or 24 is associated a locking element 30, equipped with a pressure screw 25 and being passed over said pin before it is fitted. Each locking element 30 is in the form of a sleeve or bush with at least one conical part 31 adapted to be inserted into a correspondingly conical part of the hole 28 of members 23 or 24 (not shown in FIGS. 4 and 6) in order to firmly lock said members in position on pin 20 by a wedge effect. Each element further comprises a body 25a which interlocks with a corresponding part of member 23, 24 to block its rotation about pin 20.

Members 23 and 24 are identical, with the only exception that their hook 27 is slightly different. Hook 27 of member 23 which is designed to rest behind the lamina of the vertebra (such as that of member 22) is flat and solid, whereas hook 27 of member 24, designed to rest under the pedicle of the vertebra, is provided with a slot to this effect. In accordance with the present invention, members with either open or closed backs can be produced with hooks having sizes and shapes suitable for these and other applications.

It will be noted that, for positioning purposes, the anchoring members ar provided with holes 33 and/or with dovetail indentations 34 used as holds for specially fitted gripping members, such as pliers.

Figure 8:
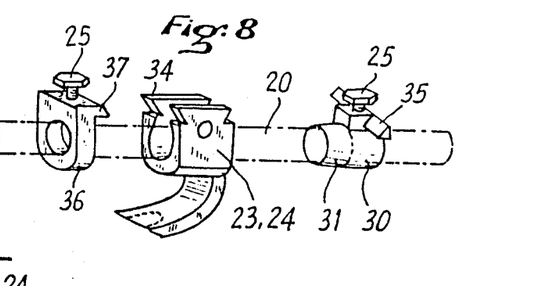

As illustrated in FIG. 8, said dovetail indentations 34 can also be used for fastening an element 23 or 24 to the pin 20, particularly when said element is required to withstand strong stresses. In this case, the locking element 30 is provided with wing members 35 adapted to engage into the facing indentations 34.

To further reinforce the joint of an element 23 or 24 with the pin 20, it is possible to provide an extra locking element 36, also shown in FIG. 8, constituted by a ring equipped with a pressure screw 25 and a projection 37, adapted to engage the indentations 34 situated on the opposite side of locking element 30.

Figure 9:
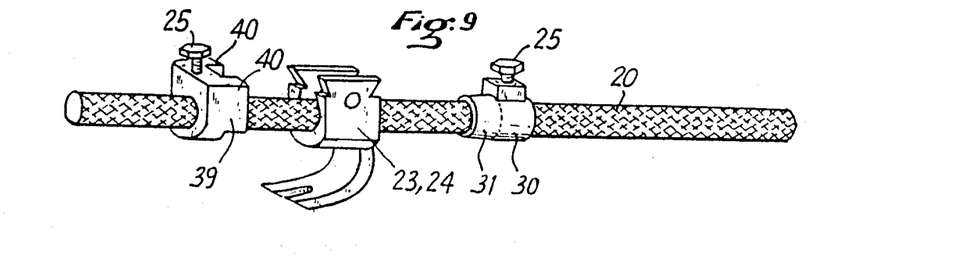

According to the variant embodiment shown in FIG. 9, a locking member is provided which comprises two side wings 40 adapted to grip the side walls of elements 23 and 24 and prevent, if necessary, said walls from moving apart. In addition, the front face of said anchoring members 23 and 24 comes to rest against a corresponding face of locking member 39, so that any pivoting movement of said members 23 and 24 is prevented, once screw 25 of member 39 is tightened.

In addition to the anchoring means described above, various other effective anchoring means can be used, such as screws and sacral staples fitted to be secured in place on the pin.

Figure 10:
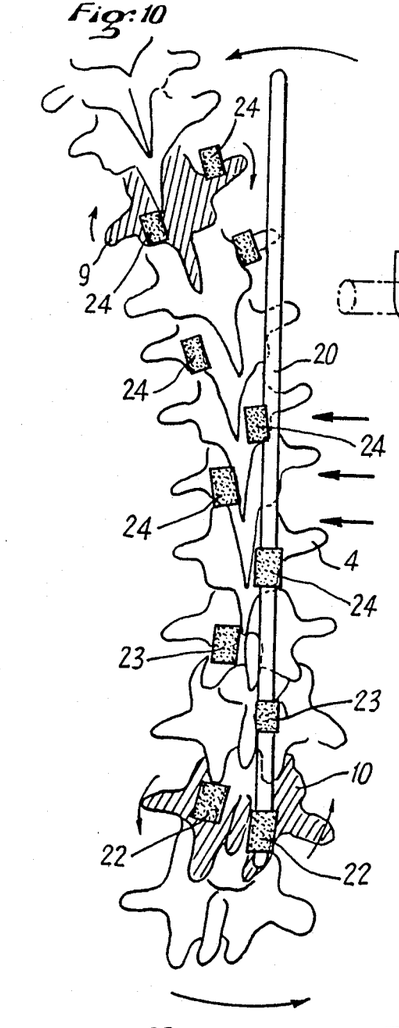
FIGS. 10, 11 and 12 illustrate a way of using the instrumentation according to the invention.
Figure 11:
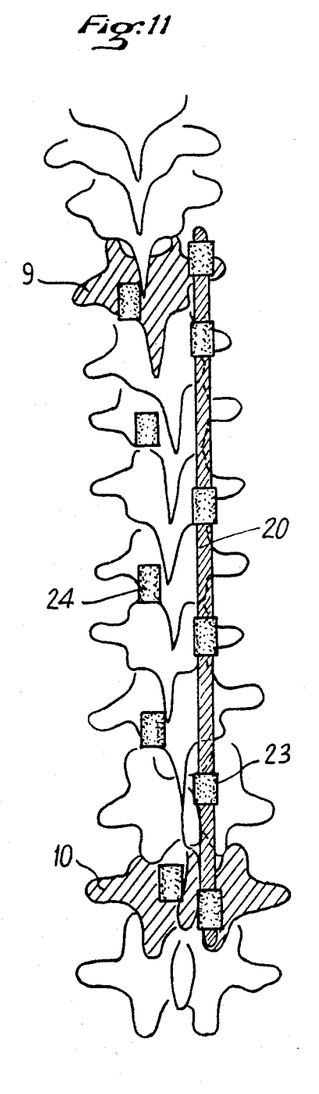
Figure 12:
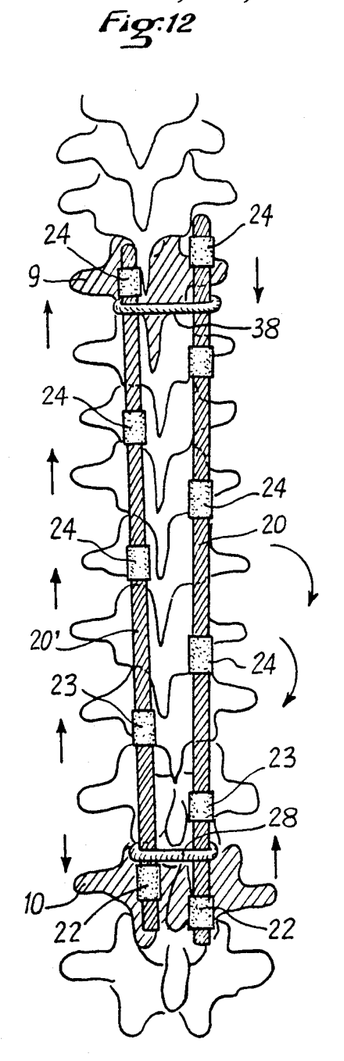

FIGS. 10, 11 and 12 illustrate a possible way to apply the device according to the invention.

First, two anchoring members 22 are positioned at the level of the lower vertebra 10, one being inserted on the lamina on the concave side, and the other under the lamina on the convex side. Then, moving upwards, either members 23 or member 24 are positioned on every other vertebra, on the concave side and on the convex side, and in such a way that said members on one side are offset with respect to the members of the other side (see FIG. 10). By bearing on the members 23 and 24 joined to the top vertebra 4, it becomes possible to proceed to at least a partial derotation of said vertebra.

Then a pin 20 is introduced into the lower member 22, on the convex side, and by using said pin as a lever, the latter is introduced successively in the members 23 and 24 which are above. This operation helps to reduce the curvature in the transverse direction, and the anchoring members of the concavity are aligned as best as they can be (see FIG. 11).

A second pin, identical to pin 20, and shown with the reference 20' in FIG. 12, is then introduced into the lower member 22 of the concavity, and having bent said pin 20' transversely if this proves necessary, the said pin is introduced successively into all the members 23 and 24 situated in the concavity of the curvature. In order to adapt to the anteroposterior physiological curvatures of the rachis, the pins may be bent within the sagittal plane without any danger of their breaking, due to their constant diameter and lack of weak points.

Members 23 and 24 of pins 20 and 20' are, of course, secured in position on said pins by way of the locking elements 30 mounted beforehand.

It will be noted that the installation of the two pins 20 and 20' tends to cause the derotation of the vertebra 4 at the peak of the curve, with respect to the extreme vertebra 9 and 10.

The installation then proceeds step-by-step, to the spreading upwardly from the middle of the curvature on the side of the concavity, of members 23 and 24 of the pin 20', and to bring closer together members 22 and 24 of pin 20 on the side of the convexity, after which all said members are fixed in position both longitudinally and rotationally by way of screws 25.

The two pins 20 and 20' are thereafter joined together by means of tractional cross-pieces 38, such as those described in my French Patent No. 73 33916 for example. In a preferred embodiment, the tractional and cross-pieces are secured to each pin by fittings comprising jaws, with the interior surfaces of the jaws being roughened to correspond to the surfaces of the pins, providing a substantially slip-proof connection when the jaws are tightened by suitable means.

After this installation, an arthrodesis is conducted according to the conventional methods.

Obviously, the installation method described with regard to FIGS. 10, 11 and 12 is only given by way of an illustration, as other methods may be used depending upon the requirements of every particular case.

Figure 13:
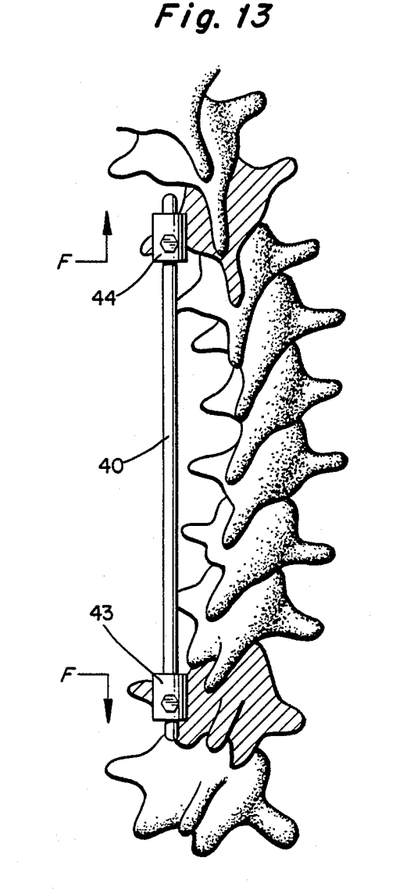
FIGS. 13 and 14 illustrate the use of a single pin system of the invention to elongate the rachis from the concavity of the curvature.
Figure 14:
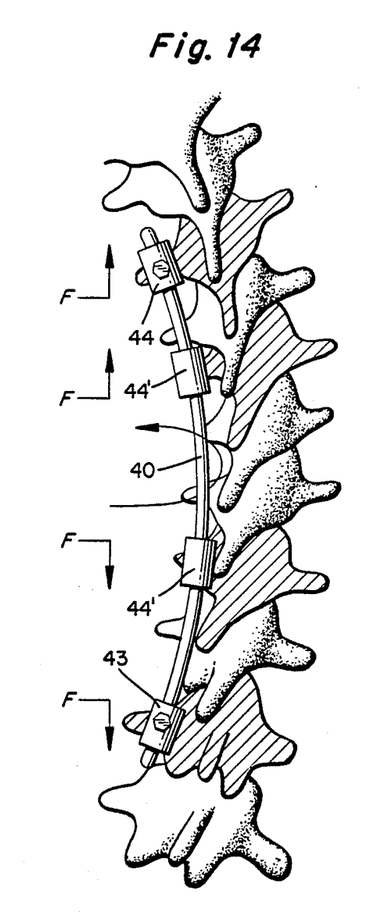

For example, in a more general application of the present invention, a device comprising a single pin 40 and at least two anchoring members 43 and 44 can be applied to the concave side of a spinal curvature to exert an elongation force, as shown in FIGS. 13 and 14, with arrows F. Although a minimum of two anchoring members 43 and 44 are required for such installations, any suitable number of members 44' can be installed to exert elongation and/or rotational forces. The vertebra upon which said members bear are shaded for clarification. The pin and anchoring members can be installed by a method substantially similar to that described for the installation of the HARRINGTON system of FIG. 3, as modified by the securing of the anchoring members described above, so that they maintain their positions on the pin, both longitudinally and rotationally. Due to the substantially constant diameter of the pin and its roughened (preferably knurled) surface, the pin can be safely bent to fit any required contour of the rachis, and the anchoring members can be used to provide both elongating and rotational forces and firmly secured in place. Proper bending of the pin is a vital step in achieving three dimensional correction of spinal deformities. A flexible pin which has been bent to fit the hooks exactly is used as a template for bending the pin to shape.

The length of a concave rod is determined initially by the distance from the upper end vertebra to the lower end vertebra, increased by the amount of the expected correction. The length of a convex rod is normally about 4 centimeters longer than that of a concave rod.

On the concave side once all the required hooks are in place and the site completely prepared, the bended pin is loaded with two hook blockers in back-to-back fashion. It is then presented to a closed pedicular hook which has been attached to the upper end vertebra, with the concavity bent into the pin in posterior position, to facilitate its introduction into the hooked anchoring member. The pin is then rotated counterclockwise 90 degrees on its axis to fit the scoliotic curve in the frontal plane, and is gently inserted into the opening of an open hooked anchoring member placed on an upper intermediate vertebra. Depending upon the situation, the pin is then inserted into either an open hook placed on a lower intermediate vertebra or closed hook of the lower end vertebra. Once the pin is in place in all the hooked anchoring members, the hook blockers are pushed into position on the intermediate vertebra. Then, the pin can be further rotated inside the hooks no tightened, but maintained in distraction by two temporary C rings (not shown) to achieve the desired corrections.

Figure 15:
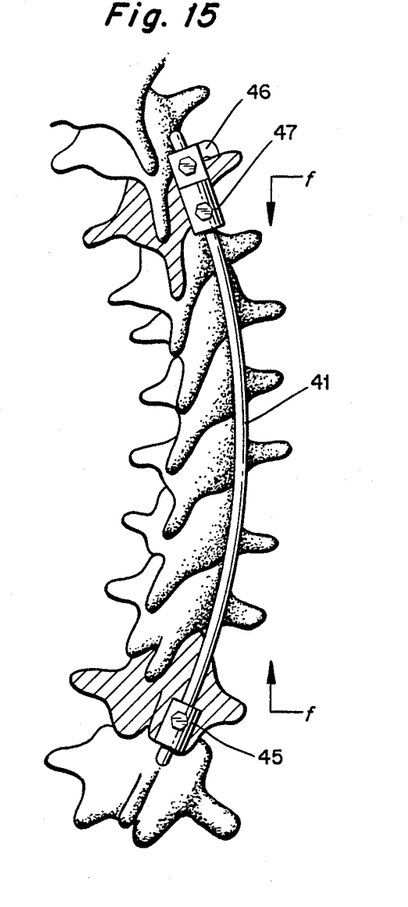
FIGS. 15 and 16 illustrate the use of a single pin system of the invention to compress the rachis from the convex side of the curvature.
Figure 16:
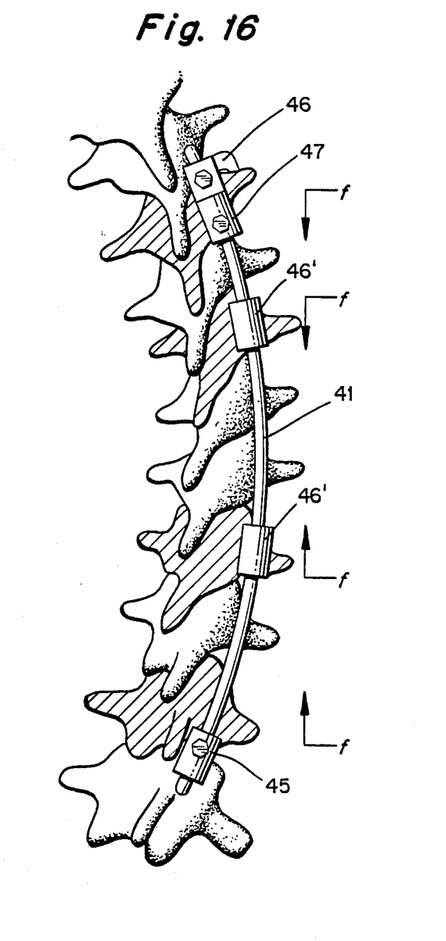

Similarly, where compressive forces and/or rotation are to be applied to the rachis, a device comprising a single pin 41 and at least two anchoring members 45 and 46 can be applied to the convex side of a spinal curvature as illustrated in FIGS. 15 and 16 by force arrows f, using an installation method similar to that described above for rod 20 in the discussion of FIGS. 10, 11 and 12.

To install such a pin on the convex side, the pin can be loaded with a locking element or "hook blocker" (not shown) directed proximally, and then presented to the two hooked members placed on the upper end vertebra (transverse and pedicular, members 46 and 47 in FIGS. 15 and 16) with the concavity of the bend posterior to facilitate insertion into these two hooks. The pin is then gently rotated to slide it into an open pedicular hook installed on the apical vertebra. The hook blocker is then introduced into the open hook to fix it in position. The lower tip of the pin is then directed into a closed laminar hook installed on the lower end vertebra, ensuring that the hook is well seated under the lamina. To introduce the pin into this lower hooked member, the pin must migrate distally. To accomplish this, an instrument is applied distally to the open apical hook and distraction is performed using a spreader. As this is done, the pi is guided into the open apical hook (by an assistant). During the process, the position of the hook under the lamina should be maintained.

The devices and installation methods of the present invention are not limited to the use of only one or two pins with their associated anchoring members. Any suitable number of pins can be used to exert the desired support and forces upon the rachis, for example, two or three pairs of shorter pins to provide localized support, installed independently or fastened together. Such pairs of pins can be installed on opposite sides, or even the same side of the rachis.

For further details of the devices and methods of the present invention, see the applicant's book, "New Instrumentation for Surgery of the Spine", to be published in French and English by Freund Publishing House, Ltd, Suite 500 Chesham House, 150 Regent Street, London, England in 1986. The devices are now available commercially as complete instrumentation systems from the Stuart Company, One Stuart Plaza, Donohue and Luxor Roads, Greensburg, Pa. 15601, and from SOFAMOR, B.P. 139, 62604 Berck-Sur Mer, Cedex, France.

Although the present invention has been described and illustrated by various preferred embodiments, it is to be considered limited only by the appended claims.

What is claimed is:

1. A device for supporting the rachis, comprising at least one pin and at least two anchoring members designed to rest on the vertebrae of said rachis and to be fixed in position on said pin, wherein said pin has a substantially constant cross-section throughout its length and has a rough surface obtained by knurling and the said anchoring members are provided with pressure means cooperating with said pin to prevent both sliding and rotational motion of said anchoring members relative to said pin.

2. A device as claimed in claim 1 wherein a single pin is employed.

3. A device as claimed in claim 1, wherein said anchoring member comprise a body provided with a through hole through which said pin is freely slidable and which is equipped with a pressure screw perpendicular to said pin and able to engage with said rough surface in order to fix said anchoring member in position on said pin and a hook integral with said body.

4. A device as claimed in claim 3 wherein at least one of said anchoring members comprises a flat, solid hook adapted to fit behind the lamina of a vertebra.

5. A device as claimed in claim 3 wherein at least one of said anchoring members comprises a slotted hook adapted to fit under the pedicle of a vertebra.

6. A device as claimed in claim 3 wherein at least one of said anchoring members has an open body comprising a groove permitting the introduction of said pin into said through hole.

7. A device as claimed in claim 1, wherein said anchoring members comprise a body with a through hole for the free passage of the rod, said hole opening onto a groove which can be traversed by said pin, and are each associated with a locking element slidable on said pin, on which it can be locked in position by means of a pressure screw, and wherein said anchoring members can be interlocked with the associated locking elements by wedging.

8. A device as claimed in claim 7, wherein an additional locking element is associated with each anchoring member, which locking element is also slidable on the pin on which it can be locked in position by means of a pressure screw, said additional locking element being placed on the side of the anchoring member opposite the normal locking element.

9. A device as claimed in claim 7, wherein said locking element comprises in addition to its wedging means, other means which are engageable in complementary parts of said anchoring member.

10. A device as claimed in claim 1, in which said pin extends over a plurality of vertebrae of the rachis, wherein a plurality of anchoring devices are mounted on said pin and distributed along the latter.

11. A device as claimed in claim 10, wherein said device comprises at least two pairs of pins which extend over a plurality of vertebra of the rachis, each pin being placed on one side thereof, and on each pin are mounted a plurality of anchoring members, wherein tractional cross-pieces are fitted between the said pins.

12. A device as claimed in claim 1 wherein said at least one pin is of circular cross-section.

13. A device for strengthening the rachis comprising at least one pin and at least two hooked anchoring members able to rest on vertebrae of said rachis and to be fixed in position on said pin, said pin being of constant cross-section throughout its length and having a rough surface obtained by knurling, wherein said anchoring members comprise a body with a through hole for the free passage of said pin, said hole opening onto a groove which can be traversed by said pin, and said anchoring members are each associated with a locking element slidable on said pin, upon which it can be locked in position by means of a pressure screw perpendicular to said pin and able to engage with said rough surface to fix said locking element in position, wherein said anchoring members can be interlocked with the associated locking elements by wedging.

14. A device as claimed in claim 13 wherein an additional locking element is associated with end anchoring member, which locking element is also slidable on the pin on which it can be locked in position by means of a pressure screw, said additional locking element being placed on the side of the anchoring member opposite the normal locking element.

15. A device as claimed in claim 13, wherein said locking element comprises in addition to its wedging means, other means which are engageable in complementary parts of said anchoring member.

16. A device as claimed in claim 13 wherein each of said pins can be bent to conform to the physiological curvatures of said rachis.

17. A device as claimed in claim 13 wherein a single pin is employed.

18. A method of installing a device for strengthening a deformed rachis having a concave and convex side, in the transverse plane, said device comprising a single pin of substantially constant cross-section which has a surface roughened by knurling and at least two hooked anchoring members mounted on said pin and each having means to selectively fix said anchoring members comprising a pressure screw perpendicular to said pin, comprising the steps of:

(a) attaching said anchoring members to vertebrae on said convex side of said rachis;

(b) inserting said pin into the lowest of said anchoring members on said convex side of said rachis;

(c) manipulating said pin so as to substantially straighten said rachis, derotate at least some of said vertebrae, and insert said pin into the remaining anchoring members on said convex side of said rachis; and (d) fixing all said anchoring members in place on said pin by tightening said pressure screws to prevent sliding and rotational motion on said pin.

19. A method as claimed in claim 18, wherein said pin is bent as required prior to step (b) to conform to the anteroposterior physiological curvatures of said rachis.

20. A method as claimed in claim 18, wherein said hooked anchoring members are further held in position by locking elements which are mounted on said pin before said pin is inserted in said anchoring members.

21. A method as claimed in claim 18 wherein said anchoring members are installed so that downward pressure is exerted upon said rachis by placing anchoring members having flat, solid hooks to rest behind the laminae of a portion of said vertebrae and upward pressure is exerted upon said rachis by placing anchoring members with slotted hooks to rest under the pedicles of a portion of said vertebrae.

22. A method of installing a device for strengthening a deformed rachis having a concave and a convex side in the transverse plane, said device comprising a single pin of substantially constant, cross-section which has a surface roughened by knurling and at least two hooked anchoring members mounted on said pin and each having means to selectively fix said anchoring members comprising a pressure screw perpendicular to said pin, comprising the steps of:

(a) attaching said anchoring members to vertebrae on said concave side of said rachis;

(b) inserting said pin into the lowest of said anchoring members on said concave side of said rachis;

(c) manipulating said pin and applying elongational force to said anchoring members so as to substantially straighten said rachis, derotate at least some of said vertebrae, and insert said pin into the remaining anchoring members on said concave side of said rachis; and (d) fixing all said anchoring members in place on said pin by tightening said pressure screws to prevent sliding and rotational motion on said pin.

23. A method as claimed in claim 22, wherein said pin is bent as required prior to step (b) to conform to the anteroposterior physiological curvatures of said rachis.

24. A method as claimed in claim 22, wherein said hooked anchoring members are further held in position by locking elements which are mounted on said pin before said pin is inserted in said anchoring members.

25. A device for strengthening the rachis comprising a single pin and at least two hooked anchoring members able to rest on vertebrae of said rachis and to be fixed on in position on said pin to prevent both sliding and rotational motion on said pin, said pin being of constant cross-section throughout its length and having a surface uniformly roughened by knurling, wherein said anchoring members comprise a body with a through hole for the free passage of said pin, said hole opening onto a groove which can be traversed by said pin, and said anchoring members are each associated with a locking element slidable on said pin, upon which it can be locked in position by means of a pressure screw perpendicular to said pin and able to engage with said roughened surface to fix said locking element in position, wherein said anchoring members can be interlocked with the associated locking elements by wedging.

* * * * *